United States Patent [19]

Fenemore et al.

[11] Patent Number: 4,752,435

[45] Date of Patent: Jun. 21, 1988

[54] SCANNING DEVICES

[75] Inventors: Peter Fenemore, Croston; Keith A. Gamble; Frank M. Hancock, both of Liverpool, all of United Kingdom

[73] Assignee: National Nuclear Corporation Limited, London, England

[21] Appl. No.: 731,512

[22] Filed: May 7, 1985

[30] Foreign Application Priority Data

May 17, 1984 [GB] United Kingdom ............... 8412608

[51] Int. Cl.$^4$ .................. G21C 17/00; G01N 29/04
[52] U.S. Cl. ...................................... 376/249; 73/623
[58] Field of Search ............... 376/245, 249; 73/590, 73/622, 623, 640

[56] References Cited

U.S. PATENT DOCUMENTS

| 4,336,104 | 6/1982 | Figlhuber et al. | 376/249 |
| 4,385,523 | 5/1983 | Gugel et al. | 376/249 |
| 4,429,329 | 1/1984 | Clemens et al. | 376/249 |
| 4,515,747 | 5/1985 | Creek et al. | 376/249 |

FOREIGN PATENT DOCUMENTS

| 495894 | 11/1938 | United Kingdom . |
| 1091528 | 11/1967 | United Kingdom . |
| 1227356 | 4/1971 | United Kingdom . |
| 1390198 | 4/1975 | United Kingdom . |
| 1489070 | 10/1977 | United Kingdom . |
| 1534726 | 12/1978 | United Kingdom . |
| 2011073 | 7/1979 | United Kingdom . |
| 2043898 | 10/1980 | United Kingdom . |
| 2088556 | 6/1982 | United Kingdom . |
| 2099581 | 12/1982 | United Kingdom . |

OTHER PUBLICATIONS

Proc. of Symp. of Inspection of UK Reactors (9/30/80) Langely et al.
Central Electricity Generating Board TV Insp. for AGR, Walton et al., p. 229, 7/79.
"Application of Robot Tech. in Insp. & Repair of Active Nuclear Plant", Lowe (1981).
"Remote Visual Inspection of AGR", IAEA Exhibit, 3/83.
"The Use of Robots & Manipulators in Hazardous Environ.", Ewen (11/30/83).
"Recent Advances in Tech. Under Sodium Inspection of LMFBR'S", McKnight et al. 4/84, Liquid Metal Engineering & Tech. in Energy Prod. Conf., Oxford, England.

Primary Examiner—Salvatore Cangialosi
Attorney, Agent, or Firm—William R. Hinds

[57] ABSTRACT

A scanning device, particularly for viewing above the core of a nuclear reactor, has links 29 pivoted together at 33 with means 35, 35a limiting relative movement in one sense. At least one link carries a transducer 36, preferably ultrasonic, for viewing. There may be two transducers arranged to view in different directions. The transducers may be mounted in a removable module.

A deployment arrangement may have a vertical hollow mast 20 down which the links can be pushed to engage a deflect element 31 to reach an arm 23 from which the links can extend as a cantilever.

16 Claims, 8 Drawing Sheets

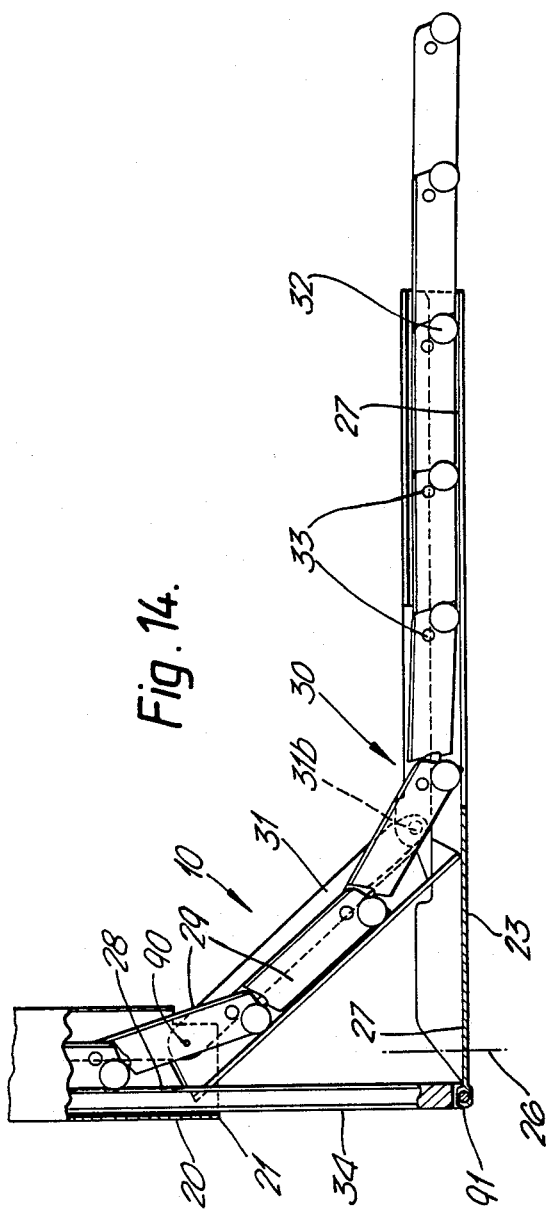
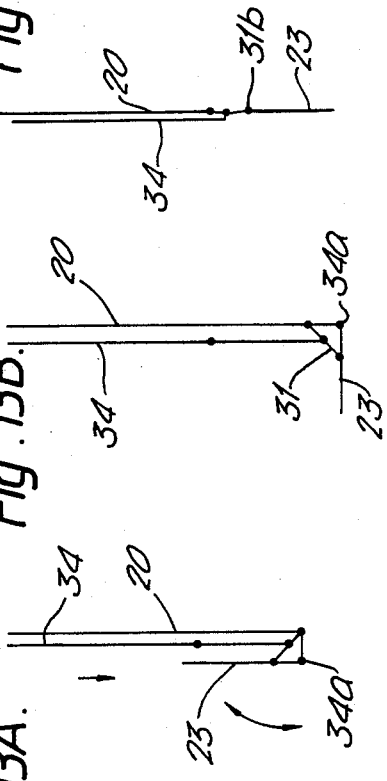

SCANNING DEVICES

This invention relates to scanning devices, particularly but not exclusively for use with nuclear reactors with particular relevance to those cooled by liquid metals.

In one aspect of the invention, there is provided a scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the ultrasonic transducer means is incorporated within the confines of the structure of at least one of said links.

Two or more links may each incorporate an ultrasonic transducer assembly within the confines of the structure thereof.

In a preferred arrangement, an ultrasonic transducer is arranged to emit ultrasound along a path extending lengthwise of the associated link, and the link incorporates reflector means located in the path of ultrasound emission for intercepting and deflecting the ultrasound beam transversely of, and beyond the confines of, the associated link.

Each such transducer-incorporating link may comprise side boundaries and upper and lower boundaries and means for routing the ultrasound generated by the respective transducer along a path of travel within the confines of the link comprising a first path component extending lengthwise of the link and a second component extending heightwise between the upper and lower boundaries of the link, the path length within the confines of the link being greater than the spacing between the upper and lower boundaries of the link and the second path component being uninterrupted by the link structure whereby the ultrasound can continue beyond the link in the direction of the second path component.

In another aspect, there is provided a scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the ultrasonic transducer means is embodied in at least one of said links and is operable to project ultrasound in opposite directions from the associated link.

In one arrangement, the ultrasonic transducer means is operable to produce two parallel beams of ultrasound which are projected lengthwise of, and within the confines of, the associated link, and the associated link includes reflector means for deflecting the incident ultrasound beams transversely of, and beyond the confines of, the associated link and in opposite directions.

In another aspect, there is provided a scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the guide arm has a base along which said links are movable, ultrasonic transducer means is mounted on two or more of said links so as to project ultrasound downwardly when the links are extended in cantilever fashion and the base of said guide arm is formed with a viewing window through which ultrasound can be projected while a link carrying a transducer means is supported on the guide arm.

In accordance with another aspect of the invention, there is provided a nuclear reactor of the liquid metal cooled fast neutron type, comprising a vessel enclosing a pool of liquid metal coolant and surmounted by a roof structure, a rotary shield mounted in said roof structure, a nuclear fuel core mounted within the vessel beneath said rotary shield, above-core structure suspended from the rotary shield and located above, and in spaced relation to, the top of the core thereby creating a gap between the core and the above-core structure, and a scanning device for inspection of the core top and the above-core structure, said scanning device comprising a hollow vertically disposed mast extending into the pool through a penetration in the rotary shield and having an exit opening immersed in the pool of coolant, the mast being rotatable about its axis, a manipulable chain structure adapted to be fed internally and lengthwise along the mast towards said exit opening, a guide arm mounted adjacent the exit opening for engaging and deflecting the chain structure generally horizontally across the core top and into said gap as the chain structure emerges at the exit opening, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm and into said gap, and ultrasonic transducer means mounted on two or more of said links and operable, when the chain structure is extended in cantilever fashion, to produce upwardly and downwardly directed beams of ultrasound from each such link.

In still another aspect, there is provided a nuclear reactor of the liquid metal cooled fast neutron type, comprising a vessel enclosing a pool of liquid metal coolant and surmounted by a roof structure, a rotary shield mounted in said roof structure, a nuclear fuel core mounted within the vessel beneath said rotary shield, above-core structure suspended from the rotary shield and located above, and in spaced relation to, the top of the core thereby creating a gap between the core and the above-core structure, and a scanning device for inspection of the core top and the above-core structure, said scanning device comprising a hollow vertically disposed mast extending into the pool through a penetration in the rotary shield and having an exit opening immersed in the pool of coolant, the mast being rotatable about its axis, a manipulable chain structure adapted to be fed internally and lengthwise along the mast towards said exit opening, a guide arm mounted adjacent the exit opening for engaging and deflecting the chain structure generally horizontally across the core top and into said gap as the chain structure emerges at the exit opening, said chain structure comprising a plurality of links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm and into said gap, and ultrasonic transducer means mounted on two or more of said links and operable, when the chain structure is extended in cantilever fashion, to produce upwardly and downwardly directed beams of ultrasound from each such link, and a nuclear reactor as claimed in claim 1 in which each transducer means is mounted within the confines of the respective link and directs ultrasound beams along parallel paths which, when the chain structure is extended in cantilever fashion, extend lengthwise and generally horizontally within the confines of the respective link, and in which each link incorporating ultrasonic transducer means also incorporates reflector elements mounted within the confines of the link to intercept respective ones of said paths and reflect the ultrasound beams upwardly and downwardly respectively.

The invention may be performed in various ways and one specific embodiment with possible modifications will now be described by way of example with reference to the accompanying drawings, in which:

FIGS. 13A to 13C show deployment of the inspection device; and

FIG. 14 is a side view of a modified arrangement.

Figure 1:
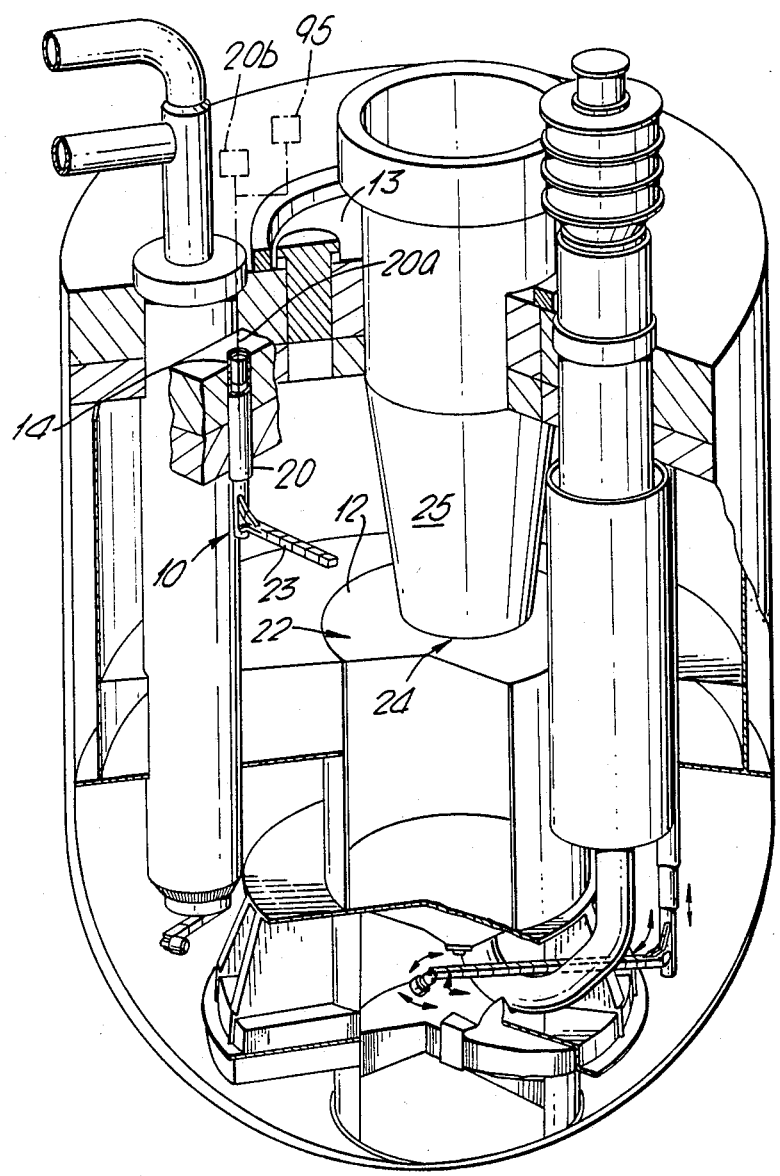
FIG. 1 is a schematic perspective view of a reactor with part cut away.

Referring to the drawings, there is shown a mechanism 10 for ultrasonic scanning of core fuel sub-assemblies 11 and other components in the vicinity of the core top 12 of a liquid metal cooled fast breeder reactor or other structure, and can be used to scan the upward facing surfaces on the fuel sub-assemblies and other core components using an undersodium viewing system. The mechanism reduces the time taken to perform the above scanning and reduces the number of movements of the reactor rotating shield 13, through which the scanning device is posted at 14 into the reactor, and which is used to traverse scanning transducers in arcuate paths over the core top 12. The mast has been shown displaced radially outwardly in FIG. 1 for clarity.

A hollow vertical mast 20 is provided which penetrates the primary containment via a penetration 14 in the reactor rotating shield 13. The bottom end 21 of the mast is located near to the periphery 22 of the core top and is fitted with an arm member 23 which is contained within the diameter of the mast for posting through the penetration in the reactor cover. Mechanisms are provided so that the arm can be deployed into a horizontal position and swept through the gap 24 between the top of the core and the underside of the above-core structure 25 by rotating the mast about the vertical axis 26 of the penetration.

The arm 23 is fitted with one or more channel tracks 27 along its longitudinal axis with a track or tracks 28 of a similar profile being provided in the vertical mast.

A series of carriages 29 which run in the tracks 27, 28 are connected end to end by means of flexible joints 30 to form a chain which can be inserted via the tracks in the mast and fed along the track(s) in the arm. Transfer of the carriages 29 from the vertical to horizontal is accomplished by means of a tracked serving link 31 pivoted at 31a to the lower end of the mast 20 and at 31b to the arm 23 and connecting the tracks in the other components.

The carriages are guided through and on the tracks by rollers 32 on both sides of each carriage, and the flexibility is provided by pivot pins 33 which join the adjacent carriages together at each end.

Movement of the carriages is effected by means of a push rod attached to the last carriage in the mast and indicated diagrammatically at 20a FIG. 1. This rod is actuated up and down by suitable means indicated diagrammatically at 20b above the shield 13 to move the horizontal carriages backwards and fowards along the arm member when deployed.

Figure 3:
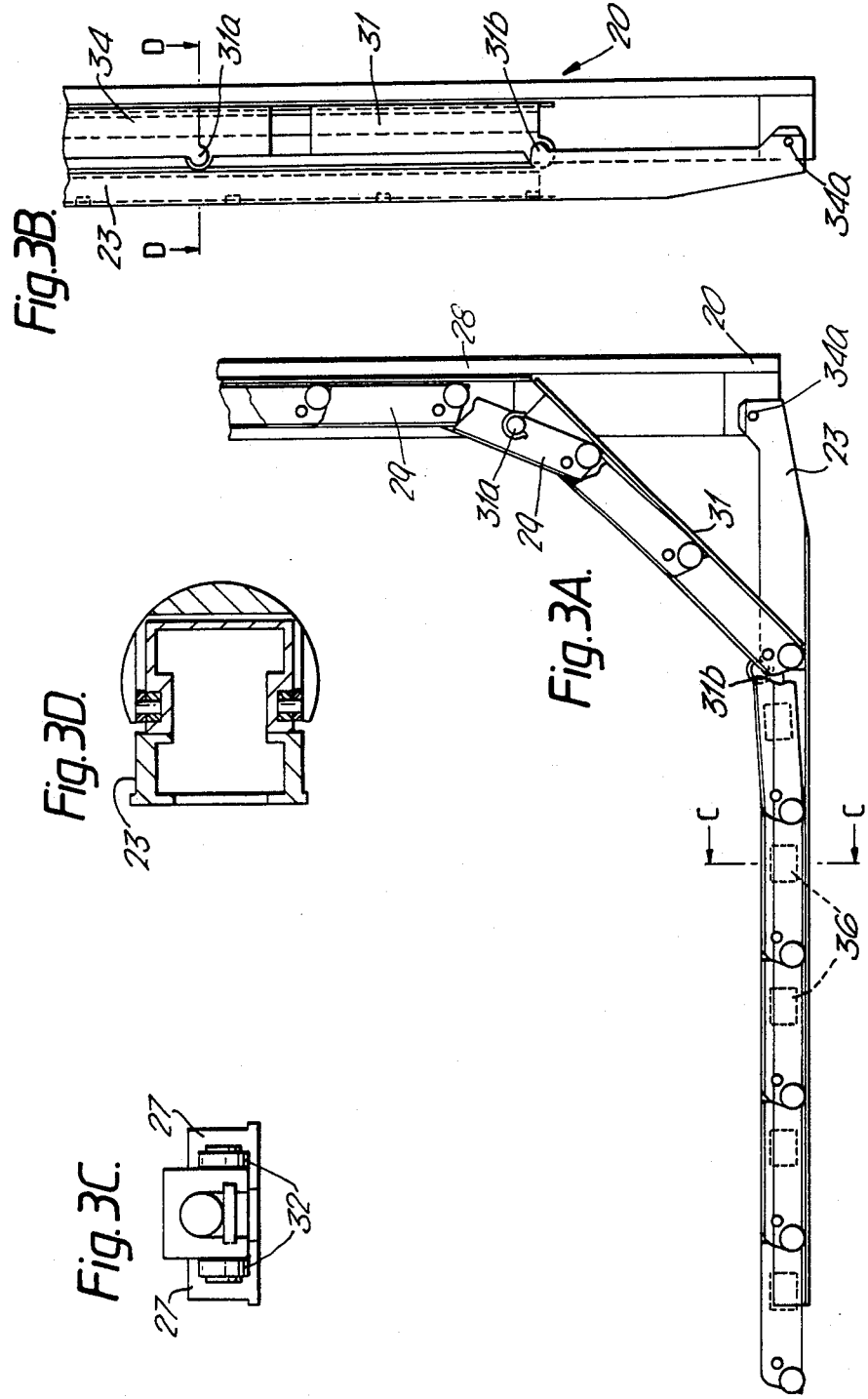
FIGS. 3A and 3B are side view of part of an inspection device in two conditions.
FIG. 3C is a section on the line C—C of FIG. 3A.
FIG. 3D is a section on the line D—D of FIG. 3B.
Figure 4:
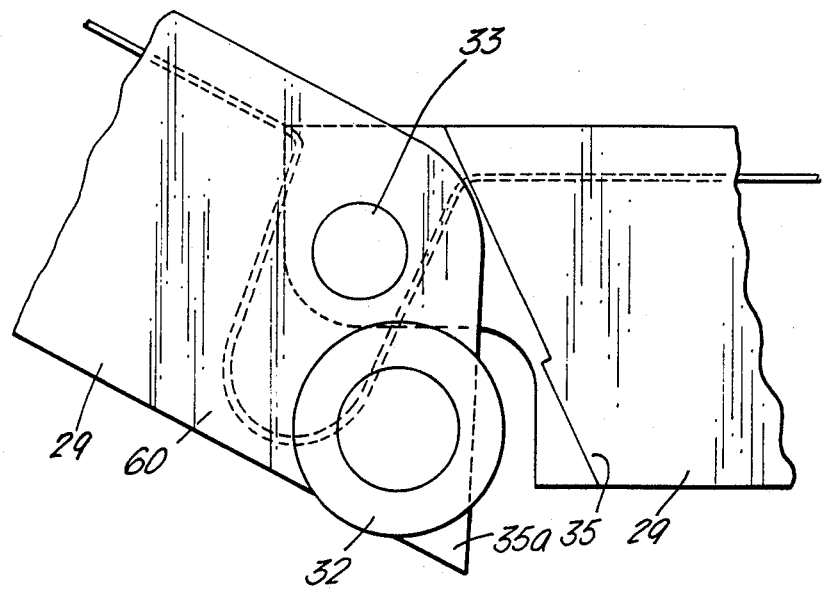
FIGS. 4 and 5 are side views of a pivot joint showing limits of relative movement.
Figure 5:
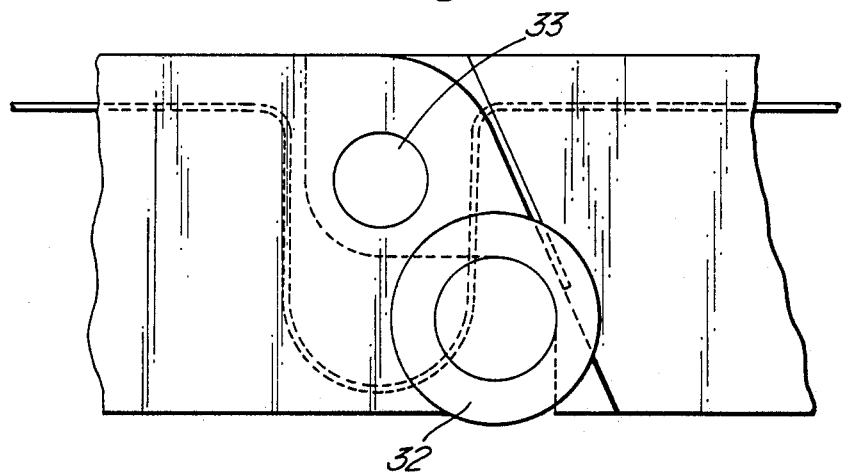
Figure 6:
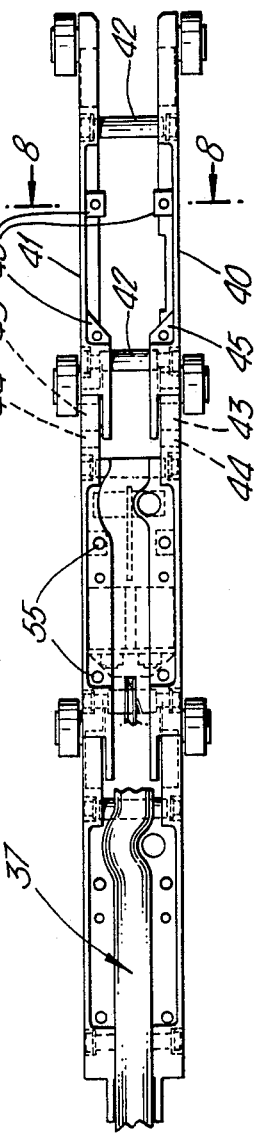
FIG. 6 is a plan view of part of a links arm.

The arrangement of the carriages and flexible joints takes the form of a laterally stiff roller chain with formations 35 at the heels of the links 29 (carriages) which engage part 35a of the adjacent link to limit pivotal movement in one sense and thus prevent the chain from drooping downwards, whilst still allowing flexibility in the upwards direction. This allows the chain to be fed vertically down the mast 20, negotiate the bend from vertical to horizontal and then extend horizontally as a stiff cantilever from the end of the arm member 23 (FIG. 3).

The carriages and flexible joints which form the links of the chain are designed to allow movement only in the upward direction as the chain is fed along the horizontal arm. The chain may be extended from the end of the horizontal arm to form a horizontal cantilever to scan areas which could not be reached if the carriages were restrained from leaving the arm.

Referring to FIGS. 6 to 9, each link 29 has a support unit or module having parallel side plates 40, 41 connected by spacer bars 42 and pivot bars 43 in bearings 44. Rollers 32 rotate on shafts 32a in plates 40, 41. The plates 40, 41 have inward lugs 45 providing apertures to enable securement of a transducer module referred to below. The support unit could be machined from a solid block rather than assembled from separate parts.

One or more ultrasonic scanning transducers 36 are mounted on a selected carriage or carriages so as to scan the core top as the carriages are actuated backwards and forwards along the arm and the arm is passed over the top of the core.

Figure 7:
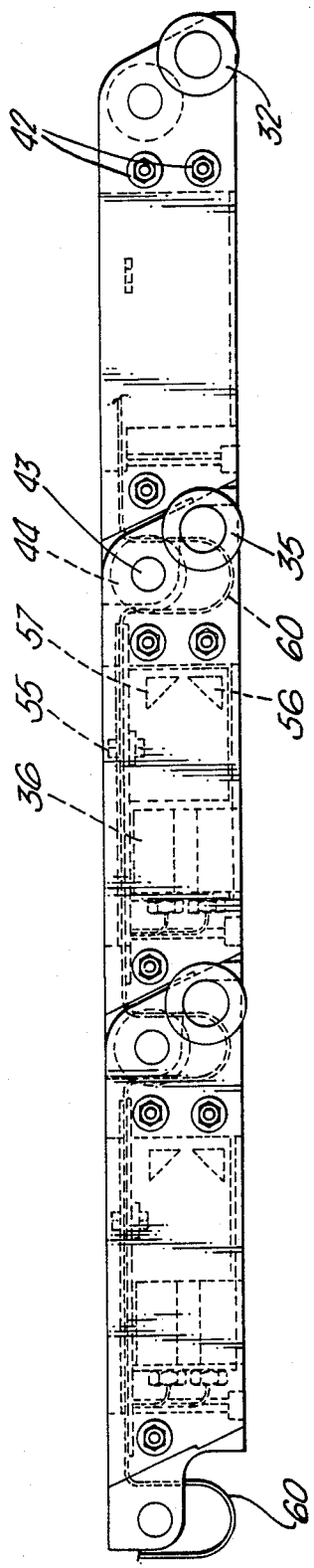
FIG. 7 is a side view of FIG. 6.
Figure 8:
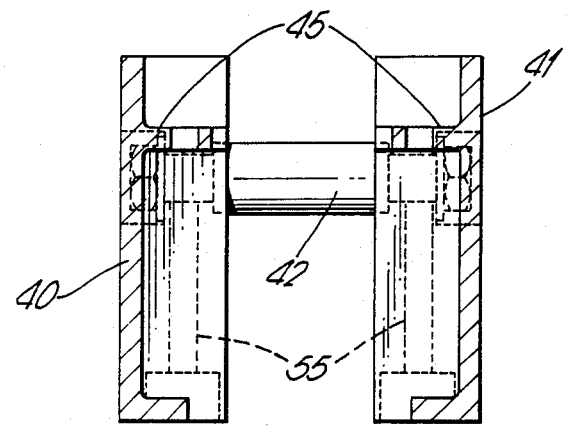
FIG. 8 is a section on the line 8—8 of FIG. 6 on a larger scale.
Figure 9:
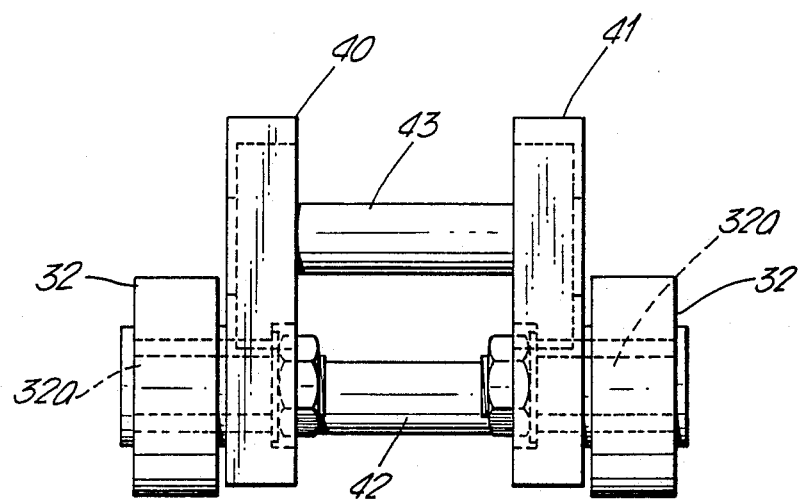
FIG. 9 is an end view from the right of FIG. 7 on a larger scale.
Figure 10:
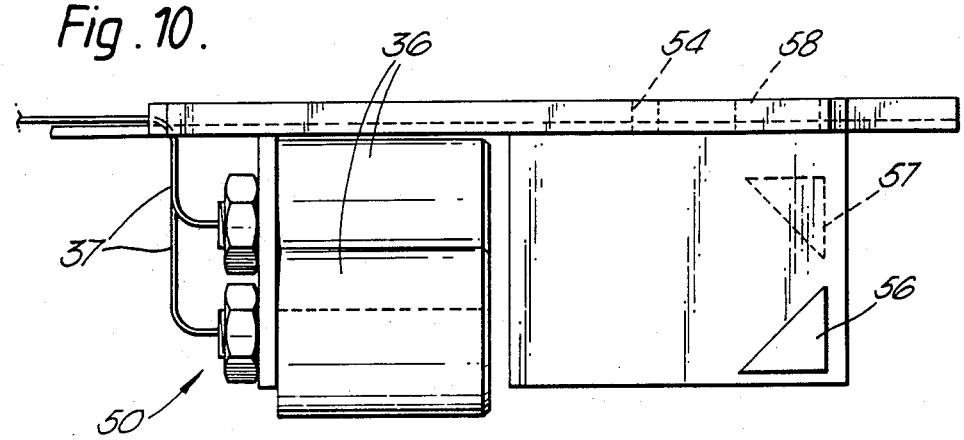
FIG. 10 is a side view of a transducer module.
Figure 11:
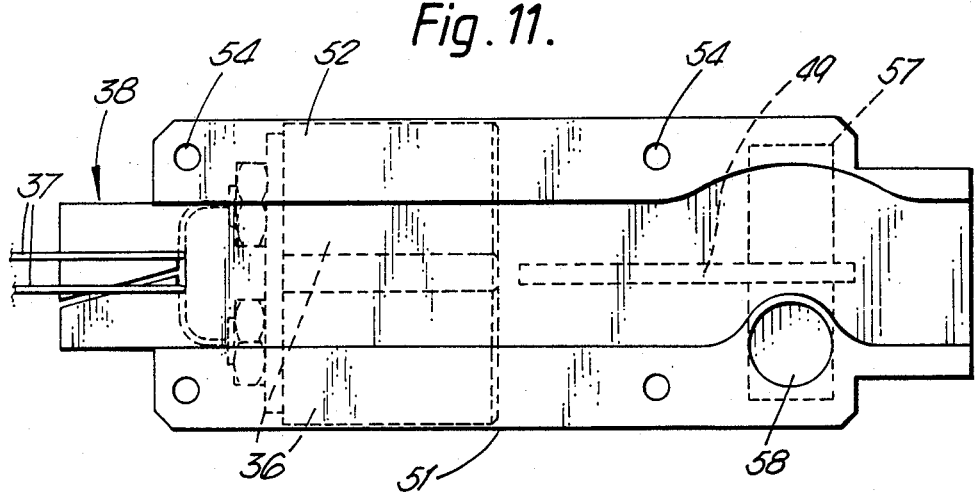
FIG. 11 is a plan view of FIG. 10.
Figure 12:
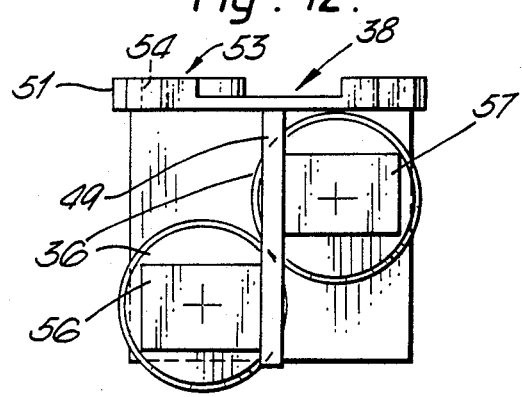
FIG. 12 is an end view from the right of FIG. 10.

In some arrangements each carriage in the chain carries at least one transducer preferably looking down; there may be two transducers, one looking up and one looking down, and this is the preferred arrangement illustrated, although for clarity one link has no transducers in FIGS. 7 and 8.

Each link has a transducer module 50 which has a top plate 53 with upper side ledges 51, 52 apertured at 54 to cooperate with apertures 45 for receipt of nuts and bolts 55 by which the module is removably mounted in the link.

The two transducers 36 are supplied through electric cables 37 and are arranged to emit beams which impinge on reflectors 56, 57 respectively arranged on opposite sides of a vertical wall 49 to direct the beam upwards and downwards, there being an aperture 58 in the top plate 53 for passage of the upward beam. Reflected beams are received by the transducers 36, via the respective reflector. The module fits between side plates 40, 41 and can readily be removed for repair.

Electrical cables 37 connecting the transducer(s) 36 to firing, signal processing, display and recording equipment indicated diagrammatically at 95 above the reactor cover 13 or remote therefrom may be routed through cable ways 38 provided along the axis of the carriages. The equipment 95 may include a display unit enabling a user to see features such as obstructions and features of the core and if the transducers produce up and down beams the equipment 95 can provide an accurate assessment of the depth of the transducer below the above-core structure in those areas where a satisfactory image can be obtained. The up and down scanning facility can be used to check the alignment between the core and the above-core components for example control and shut-off rod guides.

The cables 37 must be routed to permit relative movement between the carriages 29, and the cables 37 are bent at 60 in the region of the pivots 33 so that the cables can flex during the relative movement.

A main advantage is the mounting of the scanning transducers 36 on the links 29 of a chain actuator which can be withdrawn into the mast 20 and also from the reactor without having to remove the mast-arm system 20/23 as well. Hence low temperature transducers can be protected from high operating temperature without removing the whole mast/arm system from the reactor.

The combination of a chain actuator carrying a limited number of transducers on selected links allows limited axial movements to carry out a series of overlapping linear scans. Rotation of the mast and hence of the arm across the core top allows extensive surface scanning to be performed with minimal movement of the rotating shield.

Figure 2:
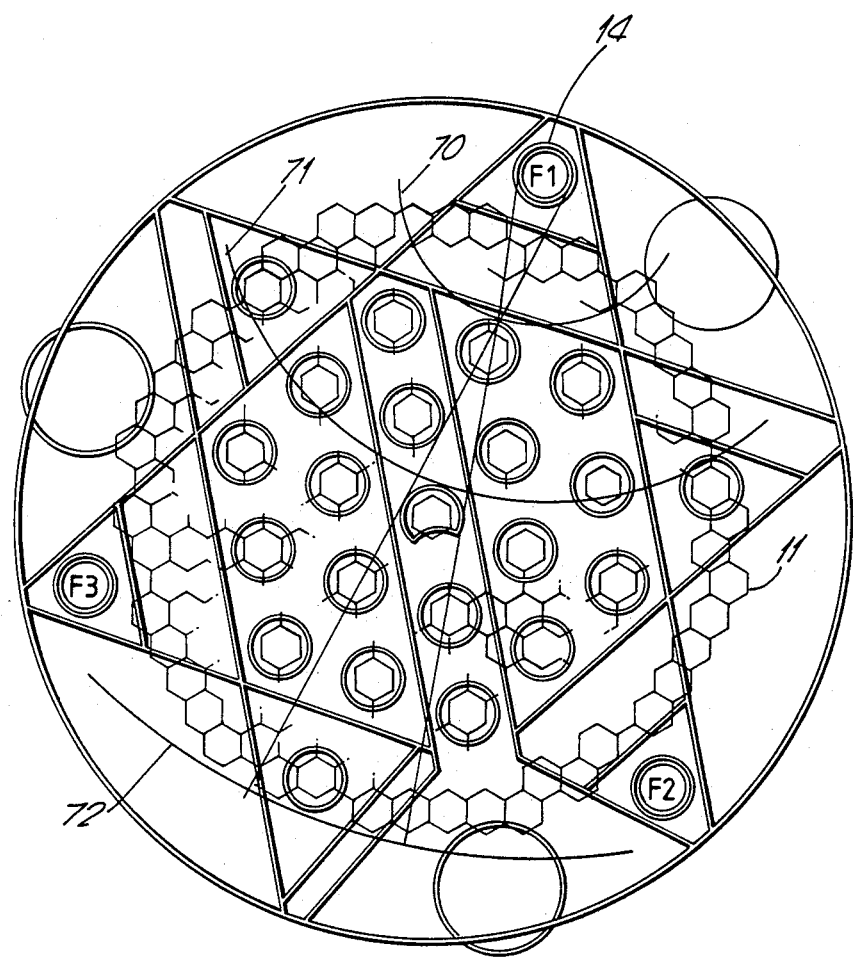
FIG. 2 is a plan view of the top of a reactor core.

Thus if the manipulable chain of carriages is posted through entry F1 FIG. 2 the chain can be extended to different extents and on rotation of the mast will scan an area having an inner limit arc 70 and an outer limit arc 72, 71 being an intermediate example in which the chain extends to the end of the arm 23. In this way all or most of the core top can be covered. If necessary the mast can be posted also at penetration F2 and/or F3 and a further scan or scans be made, or the reactor shield can be rotated to bring the position F1 to the positions F2 and F3 at which further scans are made.

The ability to extend the chain actuator as a stiff cantilever increases the range of the scanner.

The device can be present in a suitably positioned penetration, eg. F1, in the reactor while fuel and other core component handling operations are taking place. Given suitable interlocks to prevent collisions the scanner can be immediately available to confirm the absence of debris and correct alignment in the event of difficulties in the handling operations. This possibility is particularly enhanced if additional ultrasonic transducers are provided which 'look' upwards, axially or radially inwards (in front of the chain), and laterally when the chain is extended beyond the arm tracks 27. Additional viewing apertures may be provided in the sides and top and bottom of the arm tracks to allow additional scanning in these directions. The outer part of the arm 23 is open top and bottom to permit viewing.

As shown in FIG. 3 the arm is pivoted at 34a to the the mast 20 so that up and down movement of a rod 34 by suitable means forming part of device 20b moves the arm 23 between an up and a horizontal position. The rod 34 extends along the mast 20 and pivots 31a, 31b are slightly offset laterally from pivot 34a to obtain the deployment movement.

In a preferred arrangement, a means of deploying the arm member 23 into the horizontal from either up or down parking position is provided as shown in FIGS. 13A to 13C. The deployment mechanism comprises an actuating rod 34 pivoted to link 31 at 31a, the direction of deployment depending on whether the rod 34 is pushed down FIG. 13c or pulled FIG. 13a. In FIG. 13c the parked position is a continuation of mast 20 and in FIG. 13a is adjacent the mast. FIG. 14 shows an alternative in which the link 31 is pivoted at 90 to the lower end of the mast and the rod 34 is pivoted at 91 to the inner end of the arm 23 so that movement of the rod 34 moves the arm 23 between horizontal and adjacent the mast. The transducer modules are not shown in FIG. 14.

In addition to core top scanning, the device can be used to scan other reactor internal components within range of the transducers; for example, the underside of the above-core structure and/or the sub-assembly support features whilst these are exposed during fuel handling. These operations may assist in the in-service inspection of reactor components to enhance confidence in the continued safe operation at the reactor.

In a contingency, the device could be used to deploy specially designed tools and devices within reach of the chain cantilever, for example to assist with the removal of a jammed core component or handling machine.

Alternatively, it may be used to deploy pressure, flow, temperature or other testing devices within the range of the chain cantilever to improve understanding or monitoring of the reactor performance.

The arm 23 can be rotated, without deployment of the carriages 29, to detect obstructions, or confirm absence of obstructions, above the core.

In addition to deployment in the horizontal plane the cantilever may also be deployed at other angles to the mast.

We claim:

1. A nuclear rector of the liquid metal cooled fast neutron type, comprising a vessel enclosing a pool of liquid metal coolant and surmounted by a roof structure, a rotary shield mounted in said roof structure, a nuclear fuel core mounted within the vessel beneath said rotary shield, above-core structure suspended from the rotary shield and located above, and in spaced relation to, the top of the core thereby creating a gap between the core and the above-core structure, and a scanning device for inspection of the core top and the above-core structure, said scanning device comprising a hollow vertically disposed mast exending into the pool through a penetration in the rotary shield and having an exit opening immersed in the pool of coolant, the mast being rotatable about its axis, a manipulable chain structure adapted to be fed internally and lengthwise along the mast towards said exit opening, a guide arm mounted adjacent the exit opening for engaging and deflecting the chain structure generally horizontally across the core top and into said gap as the chain structure emerges at the exit opening, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm and into said gap, and ultrasonic transducer means mounted on two or more of said links and operable, when the chain structure is extended in cantilever fashion, to produce upwardly and downwardly directed beams of ultrasound from each such link.

2. A nuclear reactor as claimed in claim 1 in which said guide arm has a base along which said links are movable and the base of the guide arm is formed with an opening extending lengthwise of the arm to afford a viewing window through which said downwardly directed beams of ultrasound from the link-mounted transducer means can be projected.

3. A nuclear reactor of the liquid metal cooled fast neutron type, comprising a vessel enclosing a pool of liquid metal coolant and surmounted by a roof structure, a rotary shield mounted in said roof structure, a nuclear fuel core mounted within the vessel beneath said rotary shield, above-core structure suspended from the rotary shield and located above, and in spaced relation to, the top of the core thereby creating a gap between the core and the above-core structure, and a scanning device for inspection of the core top and the above-core structure, said scanning device comprising a hollow vertically disposed mast extending into the pool through a penetration in the rotary shield and having an exit opening immersed in the pool of coolant, the mast being rotatable about its axis, a manipulable chain structure adapted to be fed internally and lengthwise along the mast towards said exit opening, a guide arm mounted adjacent the exit opening for engaging and deflecting the chain structure generally horizontally across the core top and into said gap as the chain structure emerges at the exit opening, said chain structure comprising a plurality of links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm and into said gap, and ultrasonic transducer means mounted on two or more of said links and operable, when the chain structure is extended in cantilever fashion, to produce upwardly and downwardly directed beams of ultrasound from each such link, and in which each transducer means is mounted within the confines of the respective link and directs ultrasound beams along parallel paths which, when the chain structure is extended in cantilever fashion, extend lengthwise and generally horizontally within the confines of the respective link, and in which each link incorporating ultrasonic transducer means also incorporates reflector elements mounted within the confines of the link to intercept respective ones of said paths and reflect the ultrasound beams upwardly and downwardly respectively.

4. A scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the ultrasonic transducer means is incorporated within the confines of the structure of at least one of said links.

5. A scanning device as claimed in claim 4 in which two or more links each incorporate an ultrasonic transducer assembly within the confines of the structure thereof.

6. A scanning device as claimed in claim 4 in which said ultrasonic transducer means is arranged to emit ultrasound along a path extending lengthwise of the associated link and in which said link incorporates reflector means located in said path of ultrasound emission for intercepting and deflecting the ultrasound beam transversely of, and beyond the confines of, the associated link.

7. A scanning device as claimed in claim 6 in which each link comprises a pair of spaced side walls and upper and lower boundaries, in which said transducer means is arranged to emit ultrasound along a path which is closer to one of said boundaries than to the other boundary and in which said reflector means is arranged to deflect the ultrasound transversely towards, and beyond, said other boundary of the link.

8. A scanning device as claimed in claim 7 in which said ultrasonic transducer means comprises two transducers emitting parallel ultrasound beams, one adjacent the upper boundary of the link and the other adjacent the lower boundary, and in which the reflector means comprises a reflector element associated with each transducer and arranged to deflect the respective ultrasound beam towards and beyond the opposite boundary of the link.

9. A scanning device as claimed in claim 8 in which the link incorporating said transducers includes a central wall extending generally medially between said side walls, in which the transducers are mounted in offset relation widthwise of the link so as to emit ultrasound beams on opposite sides of said medial wall to one another and in which said reflector elements are mounted on opposite sides of said medial wall.

10. A scanning device as claimed in claim 4, each such transducer-incorporating link comprising side boundaries and upper and lower boundaries and incorporating means for routing the ultrasound generated by the respective transducer means along a path of travel within the confines of the link comprising a first path component extending lengthwise of the link and a second component extending heightwise between the upper and lower boundaries of the link, said path length within the confines of the link being greater than the spacing between the upper and lower boundaries of the link and said second path component being uninterrupted by the link structure whereby the ultrasound can continue beyond the link in the direction of said second path component.

11. A scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the ultrasonic transducer means is embodied in at least one of said links and is operable to project ultrasound in opposite directions from the associated link.

12. A scanning device as claimed in claim 11 in which the ultrasonic transducer means is operable to produce two parallel beams of ultrasound which are projected lengthwise of, and within the confines of, the associated link and in which the associated link includes reflector means for deflecting the incident ultrasound beams transversely of, and beyond the confines of, the associated link and in opposite directions.

13. A scanning device as claimed in claim 12 in which the link provided with said transducers has side boundaries and upper and lower boundaries, in which the transducers are mounted alongside each other but in transversely offset relation so that one transducer produces an ultrasound beam proximate the upper boundary and the other transducer produces an ultrasound beam proximate the lower boundary, and in which the reflector means comprises a pair of reflector elements mounted to intercept the ultrasound beam produced by a respective transducer and deflect that ultrasound beam towards and beyond the opposite one of said upper and lower boundaries whereby the reflected ultrasound beam from each transducer passes through a horizontal plane containing the incident beam from the other transducer.

14. A scanning device as claimed in claim 11 in which each link mounting a said transducer means has side boundaries and upper and lower boundaries, and including means for routing the ultrasound along a path of travel within the confines of the associated link comprising a first path component extending lengthwise of the link and a second path component extending heightwise between the upper and lower boundaries of the link, said path length within the confines of the link being greater than the spacing between the upper and lower boundaries of the link.

15. A scanning device comprising: a hollow mast having an exit opening, a manipulable chain structure adapted to be fed internally and lengthwise along the mast towards said exit opening, a guide arm mounted adjacent the exit opening for engaging and deflecting the chain structure transversely of the mast as the chain structure emerges at the exit opening, and ultrasonic transducer means carried by said chain structure, said chain structure comprising a plurality of generally similarly sized links connected pivotally together in endwise relation and means for allowing relative pivotal movement between adjacent links in one direction only when adjacent links are aligned whereby the chain structure, on engagement with the guide arm, can negotiate the resulting deflection and, following deflection, can extend transversely of the mast in cantilever fashion beyond the guide arm; characterised in that the guide arm has a base along which said links are movable, ultrasonic transducer means is mounted on two or more of said links are extended in cantilever fashion and the base of said guide arm is formed with a viewing window through which ultrasound can be projected while a link carrying a transducer means is supported on the guide arm.

16. A scanning device as claimed in claim 15 in which each ultrasonic transducer means comprises a pair of transducers incorporated within the confines of the structure of the respective link and each transducer being arranged to emit an incident beam of ultrasound within the confines of the link along a path extending lengthwise of the link and parallel to the incident beam emitted by the other transducer, and in which a pair of reflector elements are mounted within the confines of the same link so as to intercept the beam of ultrasound from a respective one of the transducers and deflect the beam transversely of and beyond the link, the reflector elements being angled to deflect the respective beams in opposite vertical directions to one another.

* * * * *